(12) United States Patent
Murayama (10) Patent No.: US 12,330,963 B2
(45) Date of Patent: Jun. 17, 2025

(54) AUTOMATIC WATER FAUCET APPARATUS

(71) Applicant: The Yokohama Rubber Co., LTD., Tokyo (JP)

(72) Inventor: Hiroshi Murayama, Kanagawa (JP)

(73) Assignee: The Yokohama Rubber Co., LTD., Tokyo (JP)

( * ) Notice: Subject to any disclaimer, the term of this patent is extended or adjusted under 35 U.S.C. 154(b) by 155 days.

(21) Appl. No.: 17/995,899

(22) PCT Filed: Jan. 7, 2021

(86) PCT No.: PCT/JP2021/000316
§ 371 (c)(1),
(2) Date: Oct. 10, 2022

(87) PCT Pub. No.: WO2021/210223
PCT Pub. Date: Oct. 21, 2021

(65) Prior Publication Data
US 2023/0202878 A1     Jun. 29, 2023

(30) Foreign Application Priority Data
Apr. 15, 2020   (JP) .................................. 2020-072851

(51) Int. Cl.
*C02F 1/32*     (2023.01)
*A61L 2/10*     (2006.01)
(Continued)

(52) U.S. Cl.
CPC .................. *C02F 1/32* (2013.01); *A61L 2/10* (2013.01); *C02F 1/008* (2013.01); *E03C 1/057* (2013.01);
(Continued)

(58) Field of Classification Search
CPC .. C02F 1/32; C02F 1/008; E03C 1/057; A61L 2/10
(Continued)

(56) References Cited

U.S. PATENT DOCUMENTS

| | | | |
|---|---|---|---|
| 2005/0001047 A1* | 1/2005 | Chamberlain | .......... F24H 1/102 |
| | | | 237/19 |
| 2018/0201516 A1 | 7/2018 | Mahdjoubi Namin | |
| 2023/0160188 A1* | 5/2023 | Waggott | .................. E03C 1/055 |
| | | | 4/222 |

FOREIGN PATENT DOCUMENTS

| | | |
|---|---|---|
| CN | 201581005 U | 9/2010 |
| CN | 201593857 U | 9/2010 |

(Continued)

*Primary Examiner* — Tuan N Nguyen
(74) *Attorney, Agent, or Firm* — Thorpe North & Western (57) ABSTRACT

An automatic water faucet apparatus includes a faucet, a detection unit, a hot water storage tank, a first ultraviolet irradiation unit, a display unit, and a control unit. The hot water storage tank heats water supplied to a water supply channel by using a heater, which is not illustrated, and stores hot water. The hot water storage tank is provided inside the faucet and heats water supplied to a second water supply channel. The first ultraviolet irradiation unit disinfects (sterilizes) the hot water stored in the hot water storage tank by irradiating the hot water with ultraviolet rays. The first ultraviolet irradiation unit includes an ultraviolet lamp disposed inside the hot water storage tank, and irradiation of ultraviolet rays to the hot water stored in the hot water storage tank and stop of the irradiation are controlled by the control unit.

13 Claims, 9 Drawing Sheets

(51) Int. Cl.
*C02F 1/00* (2023.01)
*E03C 1/05* (2006.01)

(52) U.S. Cl.
CPC ........ *A61L 2202/11* (2013.01); *A61L 2202/14* (2013.01); *C02F 2201/326* (2013.01); *C02F 2307/06* (2013.01); *E03C 2201/40* (2013.01)

(58) Field of Classification Search
USPC ... 4/623, 625, 626, 638, 675–678, 668, 222, 4/900
See application file for complete search history.

(56) References Cited

FOREIGN PATENT DOCUMENTS

| | | | | |
|---|---|---|---|---|
| CN | 203653278 U | | 6/2014 | |
| CN | 109973716 A | * | 7/2019 | |
| DE | 102016110061 A1 | | 11/2017 | |
| JP | 10-338952 A | | 12/1998 | |
| JP | 11-36394 A | | 2/1999 | |
| JP | H11-36394 A | | 2/1999 | |
| JP | 2003-106662 A | | 4/2003 | |
| JP | 2006-132277 A | | 5/2006 | |
| JP | 2006-274573 A | | 10/2006 | |
| JP | 3222747 U | | 8/2019 | |
| KR | 20030077823 A | | 10/2003 | |
| WO | WO-2013167898 A1 | * | 11/2013 | ............... A61L 2/10 |
| WO | WO 2014141693 A1 | | 9/2014 | |
| WO | WO 2018/097786 A1 | | 5/2018 | |
| WO | WO 2019/055348 A1 | | 3/2019 | |

\* cited by examiner

AUTOMATIC WATER FAUCET APPARATUS

TECHNICAL FIELD

The present technology relates to an automatic water faucet apparatus suitable for an aircraft lavatory unit and the like.

BACKGROUND ART

An automatic water faucet apparatus that detects part of a human body (finger) to discharge and stop water from a water discharge port of a faucet has been provided.

Such an automatic water faucet apparatus that has been provided includes a hot water storage tank that heats water supplied to a water supply channel communicating with a water discharge port and stores hot water, allowing the hot water to be used.

Unfortunately, when such an automatic water faucet apparatus is applied to, for example, an aircraft lavatory unit, the hot water will be stored in the hot water storage tank for a long time unless the automatic water faucet apparatus is used for a long time. Accordingly, there is a concern that various bacteria may grow in the hot water for some reason.

SUMMARY

The present technology provides an automatic water faucet apparatus advantageous in maintaining hygiene of hot water stored in a hot water storage tank.

An embodiment of the present technology is an automatic water faucet apparatus configured to discharge and stop water by detecting part of a human body. The automatic water faucet apparatus includes a faucet including a water discharge port and configured to be attached to a sink, a hot water storage tank configured to heat water supplied to a water supply channel communicating with the water discharge port and store hot water, and a first ultraviolet irradiation unit configured to irradiate the hot water stored in the hot water storage tank with ultraviolet rays.

According to an embodiment of the present technology, a first ultraviolet irradiation unit configured to irradiate the hot water stored in a hot water storage tank with ultraviolet rays is provided, allowing bacteria in the hot water stored in the hot water storage tank to be prevented from growing, and it is advantageous in maintaining hygiene of the hot water.

DETAILED DESCRIPTION

First Embodiment

Next, the present embodiment will be described with reference to the drawings.

First, an aircraft lavatory unit to which an automatic water faucet apparatus according to the present embodiment is applied will be described.

Figure 1:
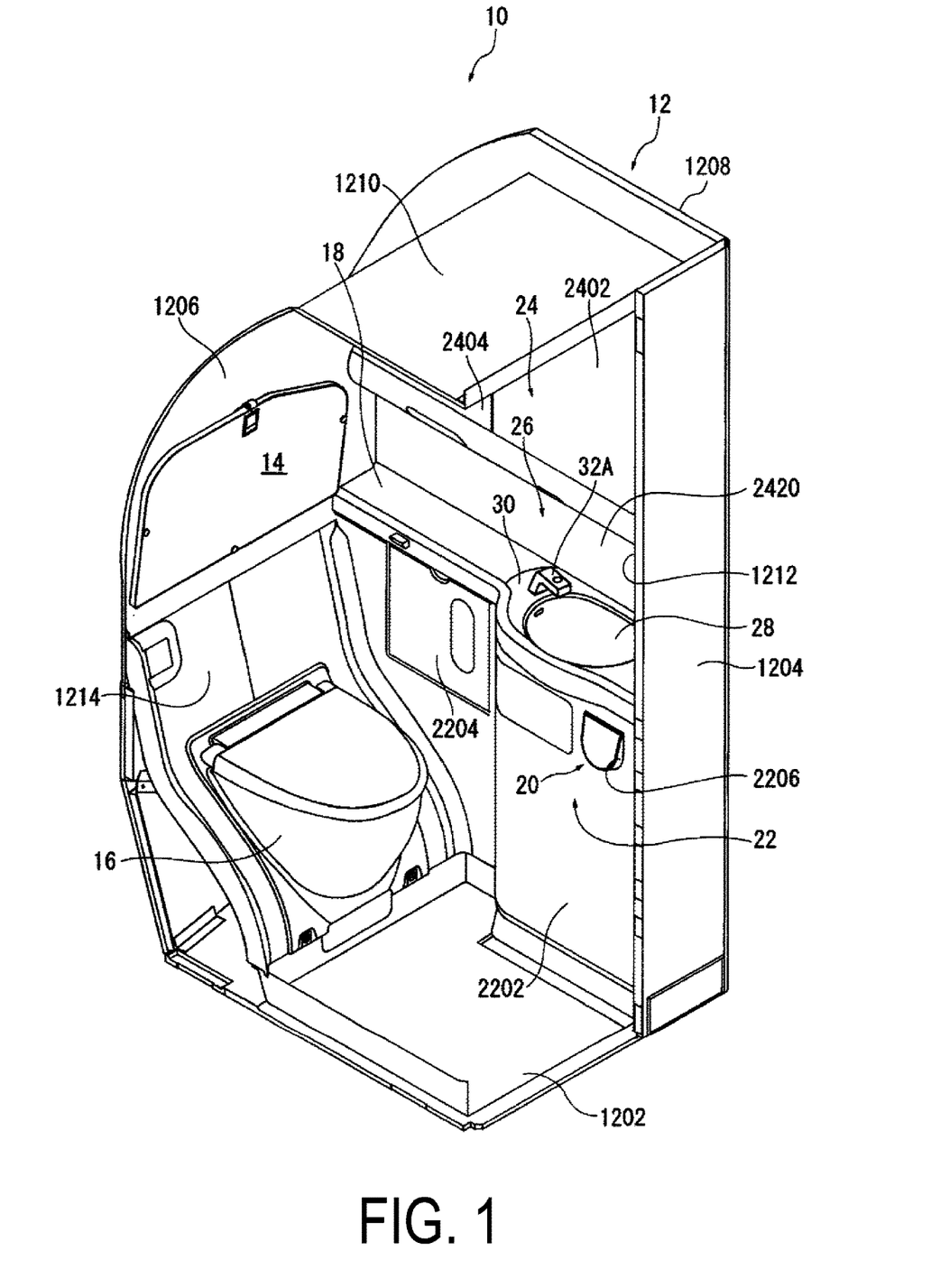
FIG. 1 is a perspective view of an aircraft lavatory unit to which an automatic water faucet apparatus according to a first embodiment is applied.

As illustrated in FIG. 1, an aircraft lavatory unit 10 includes a structural frame 12 including a bottom wall 1202, a plurality of wall plates rising from the bottom wall 1202, and a ceiling 1210 that form a lavatory 14 therein.

In the present embodiment, one of the plurality of wall plates is a front wall 1204, one is a rear wall 1206 facing the front wall 1204, and the remaining two walls are a pair of side walls 1208 that connect two sides of the rear wall 1206 and corresponding two sides of the front wall 1204, an entrance 1212 opened and closed by a door is provided on the front wall 1204, an inner wall 1214 is provided in front of the rear wall 1206, and a toilet 16 is provided on the bottom wall 1202 via the inner wall 1214.

Note that in FIG. 1, one side wall 1208 of the pair of side walls 1208, and the door that opens and closes the entrance are omitted.

A counter table 18 is provided in the middle of the other side wall 1208 of the pair of side walls 1208 in the height direction. Below the counter table 18 is a lower storage portion 22 for storing a trash can device 20 with a fire extinguishing function, equipment for the lavatory 14, and the like. The lower storage portion 22 can be opened and closed by a plurality of doors 2202 and 2204. In FIG. 1, the reference sign 2206 indicates a trash feeding port.

Above the counter table 18 is an upper storage portion 24 for storing the equipment for the lavatory 14, such as tissues. The upper storage portion 24 is opened and closed by a plurality of mirrored doors 2402 and 2404.

A wash basin 26 is provided at a location of the counter table 18 near the front wall 1204.

The wash basin 26 includes a hand wash bowl 28, a sink 30 configured at a location of the counter table 18 around the hand wash bowl 28, and an automatic water faucet apparatus 32A that is provided on the sink 30 and enables water discharge into the hand wash bowl 28.

The automatic water faucet apparatus 32A detects part of a human body (fingers) to discharge and stop water.

As illustrated in FIGS. 2A, 2B, 2C, and FIG. 3, the automatic water faucet apparatus 32A includes a faucet 34, a detection unit 36, a hot water storage tank 38, a first ultraviolet irradiation unit 40, a display unit 42, and a control unit 44.

Figure 2A:
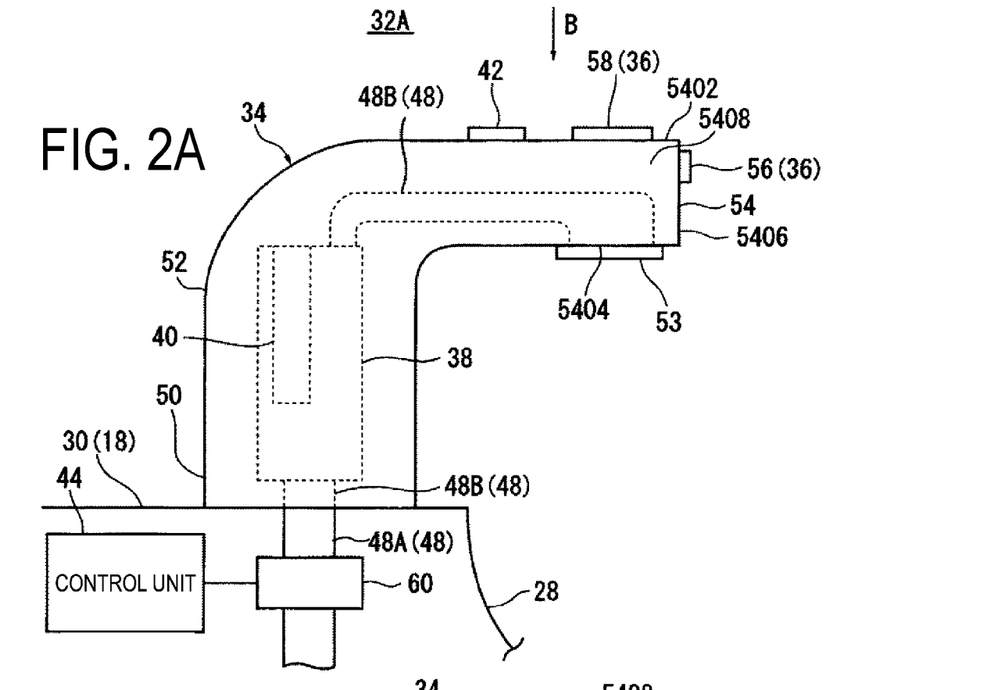
FIG. 2A is a side view of the automatic water faucet apparatus according to the first embodiment.

The faucet 34 discharges water supplied from a water supply source 46 via a water supply channel 48.

As illustrated in FIG. 2A, the water supply channel 48 includes a first water supply channel 48A that is connected to the water supply source 46 and located outside the faucet 34, and a second water supply channel 48B that is provided inside the faucet 34 and connects the first water supply channel 48A and a water discharge port 53 described below.

The faucet 34 is made of various known materials such as metal and synthetic resin.

Figure 2B:
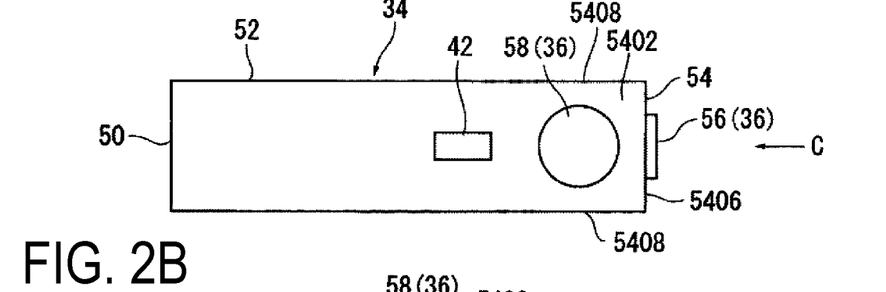
FIG. 2B is a view in the direction of arrow B in FIG. 2A.
Figure 2C:
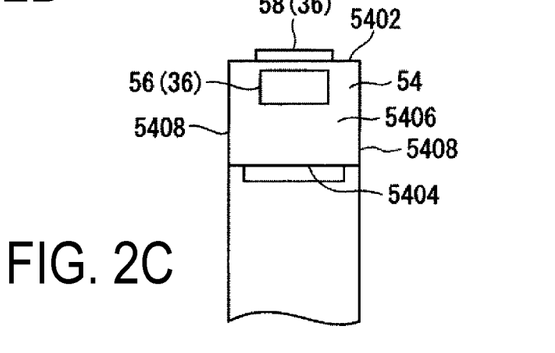
FIG. 2C is a view in the direction of arrow C in FIG. 2B.

As illustrated in FIGS. 2A, 2B and 2C, the faucet 34 includes a base portion 50 attached to an upper surface of the sink 30 or a wall portion in the vicinity of the sink 30 (in the present embodiment, for example, a wall portion 2420 that connects between the counter table 18 and the upper storage portion 24), an extending portion 52 extending above the hand wash bowl 28 from the base portion 50, and a water discharge portion 54 that is provided on a tip portion extending in a substantially horizontal direction of the extending portion 52 and includes the water discharge port 53 directed to the inside of the hand wash bowl 28.

The water discharge portion 54 includes an upper surface 5402 facing upward, a lower surface 5404 facing downward, that is, facing to the inside of the hand wash bowl 28, a front surface 5406 facing forward, and a pair of left and right side surfaces 5408 connecting the upper surface 5402, the lower surface 5404, and the front surface 5406, and the water discharge port 53 is provided on the lower surface 5404.

Thus, the water discharge port 53 is provided at a location separated upward from the hand wash bowl 28.

Figure 3:
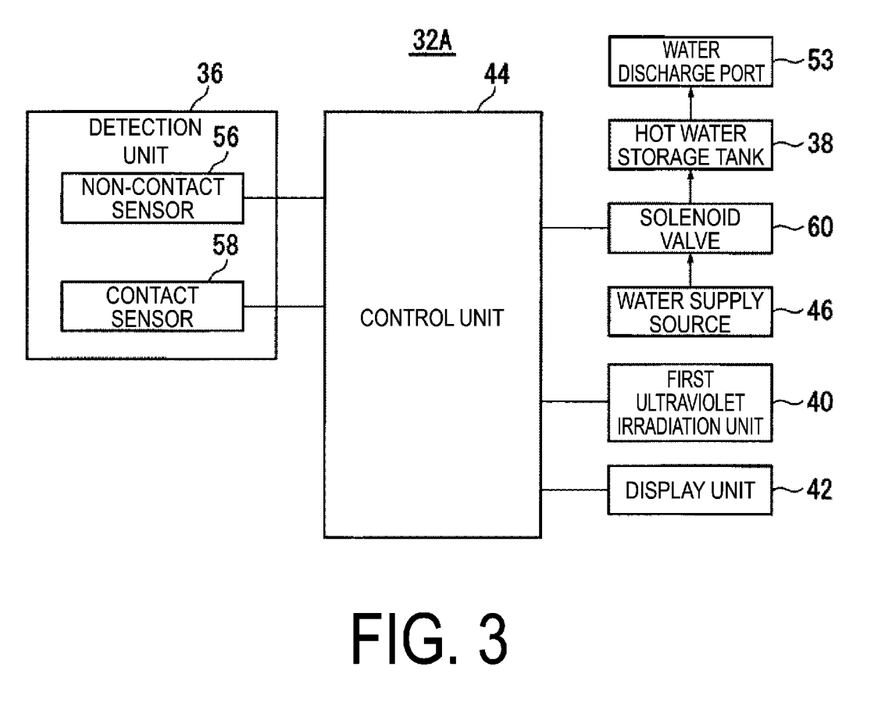
FIG. 3 is a block diagram illustrating a configuration of a control system of the automatic water faucet apparatus according to the first embodiment.

The detection unit 36 detects part of a human body.

In the present embodiment, the detection unit 36 includes two sensors, a non-contact sensor 56 and a contact sensor 58.

The non-contact sensor 56 detects part of a human body in a non-contact manner. The non-contact sensor 56 can use a known sensor such as an infrared sensor that irradiates part of a human body with detection light composed of infrared rays and detects the part of the human body based on reflected light or a capacitive non-contact sensor that detects part of a human body in a non-contact manner with a change in electrostatic capacitance due to the approach of the part of the human body.

In the present embodiment, the non-contact sensor 56 is an infrared sensor and is provided on the front surface 5406 of the water discharge portion 54.

The non-contact sensor 56 is designed to irradiate the forward of the water discharge portion 54 with detection light and reliably irradiate fingers of a user inserted in the hand wash bowl 28 with the detection light.

The contact sensor 58 detects part of a human body when contacted by the part of the human body. The contact sensor 58 can use a known sensor such as a touch switch that detects finger contact or a capacitive touch sensor that detects part of a human body with a change in capacitance due to finger contact.

In the present embodiment, the contact sensor 58 is a touch switch and is provided on the upper surface 5402 of the water discharge portion 54.

The contact sensor 58 projects upward from the upper surface 5402 of the water discharge portion 54 and is designed to allow a finger of a user to easily contact the contact sensor 58.

As described above, the detection unit 36 includes the non-contact sensor 56 and the contact sensor 58, allowing the user to selectively use the non-contact sensor 56 or the contact sensor 58 and improving usability.

It is needless to say that the detection unit 36 may be constituted by any one of the non-contact sensor 56 and the contact sensor 58.

The hot water storage tank 38 heats water supplied to the water supply channel 48 by using a heater, which is not illustrated, and stores hot water. In the present embodiment, the hot water storage tank 38 is provided inside the base portion 52 of the faucet 34 and heats water supplied to the second water supply channel 48B.

The capacity of the hot water to be stored in the hot water storage tank 38 is, for example, a minimum capacity sufficient to wash a user's hands, and thus consumption of the hot water is reduced.

The first ultraviolet irradiation unit 40 irradiates the hot water stored in the hot water storage tank 38 with ultraviolet rays to disinfect (sterilize) the hot water.

In the present embodiment, the first ultraviolet irradiation unit 40 includes an ultraviolet lamp disposed inside the hot water storage tank 38, and irradiation of ultraviolet rays to the hot water stored in the hot water storage tank 38 and stop of the irradiation are controlled by the control unit 44 described below:

The display unit 42 indicates that the first ultraviolet irradiation unit 40 is irradiating the hot water stored in the hot water storage tank 38 with ultraviolet rays, and in the present embodiment, the display unit 42 is provided side by side with the contact sensor 58 at a location behind the contact sensor 58 on the upper surface 5402 of the water discharge portion 54.

The display unit 42 includes an LED (light emitting diode) lamp, and lighting of the LED lamp indicates that hot water is being irradiated with ultraviolet rays, and turning off of the LED lamp indicates that the irradiation of the hot water with ultraviolet rays is stopped.

The control unit 44 may be provided in the faucet 34, but in the present embodiment, the control unit 44 is provided at a location below the counter table 18 in the vicinity of the faucet 34.

The control unit 44 is connected to the detection unit 36 via a cable, which is not illustrated, and switches between discharge and stop of water from the water discharge port 53 based on a detection signal supplied via the cable.

As illustrated in FIGS. 2A-2C, in the present embodiment, a solenoid valve 60 is provided at a location of the first water supply channel 48A between the water supply source 46 and the hot water storage tank 38. When the control unit 44 receives the detection signal indicating that part of a human body is detected by the detection unit 36, the solenoid valve 60 is opened for a first predetermined time, which is preliminarily set, to cause water to be discharged from the water discharge port 53, and the solenoid valve 60 is closed when the first predetermined time has elapsed.

In this manner, by opening the valve for the first predetermined time, a predetermined amount of water, which is the water corresponding to the capacity of the hot water storage tank 38 in the present embodiment, is supplied to the hot water storage tank 38. Accordingly, the hot water in the hot water storage tank 38 is discharged from the faucet 34.

Further, the control unit 44 controls the first ultraviolet irradiation unit 40 to irradiate ultraviolet rays to the hot water in the hot water storage tank 38 and to stop the irradiation, based on the detection signal output from the detection unit 36.

In the present embodiment, the control unit 44 is configured to cause the first ultraviolet irradiation unit 40 to perform irradiation of ultraviolet rays for a second predetermined time with water from the water discharge port 53 stopped. This second predetermined time is set to time sufficient for sufficiently disinfecting the hot water in the hot water storage tank 38.

Furthermore, the control unit 44 lights the display unit 42 during the second predetermined time at which the hot water in the hot water storage tank 38 is being irradiated with ultraviolet rays by the first ultraviolet irradiation unit 40, and indicates that irradiation of ultraviolet rays to the hot water in the hot water storage tank 38 by the first ultraviolet irradiation unit 40 is being performed. When the second predetermined time has elapsed, the control unit 44 turns off the display unit 42 and indicates that irradiation of ultraviolet rays to the hot water in the hot water storage tank 38 by the first ultraviolet irradiation unit 40 is stopped.

Figure 4:
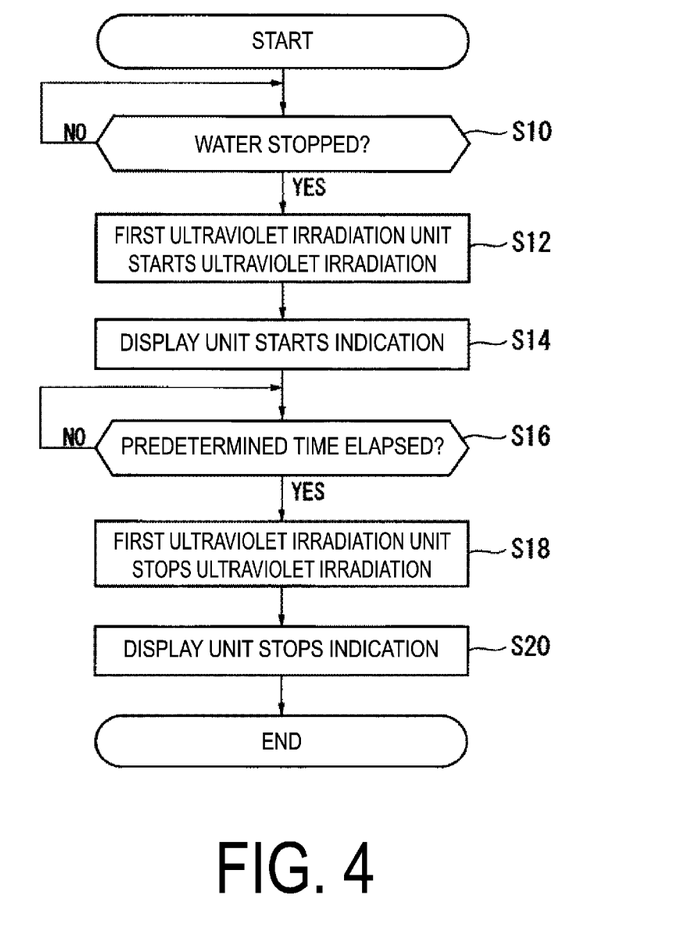
FIG. 4 is a flow chart illustrating an operation of the automatic water faucet apparatus according to the first embodiment.

Next, control of the first ultraviolet irradiation unit 40 by the control unit 44 is described with reference to the flow chart of FIG. 4.

First, the control unit 44 determines whether water is stopped based on presence of the detection signal from the detection unit 36 (step S10). In other words, when the detection signal indicating that the part of the human body is detected is received from the detection unit 36, the solenoid valve 60 is opened, and thus water is being discharged, and when the detection signal is not received, the solenoid valve 60 is closed, and thus water is stopped.

When YES is determined in step S10, water is stopped and the hot water stored in the hot water storage tank 38 is stagnant, and thus irradiation of ultraviolet rays to the hot water in the hot water storage tank 38 by the first ultraviolet irradiation unit 40 is performed (step S12).

When NO is determined in step S10, water is being discharged, and an effect of disinfection is less effective even when the hot water flowing from the hot water storage tank 38 toward the water discharge port 53 is irradiated with ultraviolet rays. Thus, the process returns to step S10 without performing ultraviolet irradiation.

Further, the control unit 44 lights the display unit 42 at the same time as irradiation of ultraviolet rays to the hot water in the hot water storage tank 38 by the first ultraviolet irradiation unit 40, and causes the display unit 42 to indicate that the hot water is being irradiated with ultraviolet rays (step S14).

Next, the control unit 44 determines whether the irradiation of ultraviolet rays by the first ultraviolet irradiation unit 40 has performed for the second predetermined time (step S16).

When NO is determined in step S16, the control unit 44 returns to step S16 and the irradiation of ultraviolet rays continues.

When YES is determined in step S16, the control unit 44 causes the first ultraviolet irradiation unit 40 to stop the irradiation of ultraviolet rays (step S18), at the same time causes the display unit 42 to stop the indication (step S20), and terminates a series of operations.

Note that in the present embodiment, every time the water is stopped, the first ultraviolet irradiation unit 40 irradiates the hot water in the hot water storage tank 38 with ultraviolet rays and disinfects the hot water in the hot water storage tank 38.

However, when it is expected that water is not discharged for a long time after this disinfection is completed and the water is stopped for a long time, it is preferable to mandatorily disinfect the inside of the hot water storage tank 38.

In this case, the control unit 44 may determine whether duration of the state of water stopped has passed a third predetermined time, which is preliminarily set. When determining that the third predetermined time has elapsed, the control unit 44 only needs to perform the processes of from steps S12 to S20. Such processes are advantageous in reliably disinfecting the hot water when the hot water is stored in the hot water storage tank 38 for a long time.

According to the present embodiment, in the automatic water faucet apparatus 32A that discharges and stops water by detecting part of a human body, the first ultraviolet irradiation unit 40 that irradiates the hot water stored in the hot water storage tank 38 with ultraviolet rays is provided, allowing bacteria in the hot water stored in the hot water storage tank 38 to be prevented from growing and advantageously maintaining hygiene of the hot water.

Further, applying this automatic water faucet apparatus 32A to the aircraft lavatory unit 10 is advantageous in maintaining and managing hygienic environment of the aircraft lavatory unit 10 and in increasing product value of the aircraft lavatory unit 10.

Further, according to the present embodiment, since the hot water storage tank 38 that heats the water supplied to the second water supply channel 48B is provided inside the faucet 34, it is not necessary to separately handle the hot water storage tank 38 and the faucet 34. Accordingly, it is advantageous in simplifying attachment and detachment of the automatic water faucet apparatus 32A.

Further, in the present embodiment, the first ultraviolet irradiation unit 40 is configured to perform irradiation of ultraviolet rays for a predetermined time when the water discharge port 53 stops water, advantageously and efficiently disinfecting the hot water by ultraviolet rays.

Further, in the present embodiment, since the display unit 42 that indicates that the hot water in the hot water storage tank 38 is being irradiated with ultraviolet rays by the first ultraviolet irradiation unit 40 is provided, the user can visually recognize the display unit 42 and understand that the hot water is being disinfected. Accordingly, the user can be encouraged to use the automatic water faucet apparatus 32A after the indication by the display unit 42 has stopped. Accordingly, the automatic water faucet apparatus 32A can be used after confirming the hot water in which hygiene is maintained, which is advantageous in improving convenience.

Second Embodiment

Next, a second embodiment will be described with reference to FIGS. 5 to 9.

Note that, in the embodiments described below, elements and members identical or similar to those of the first embodiment have reference signs identical to those of the first embodiment, and descriptions thereof are omitted.

Figure 5:
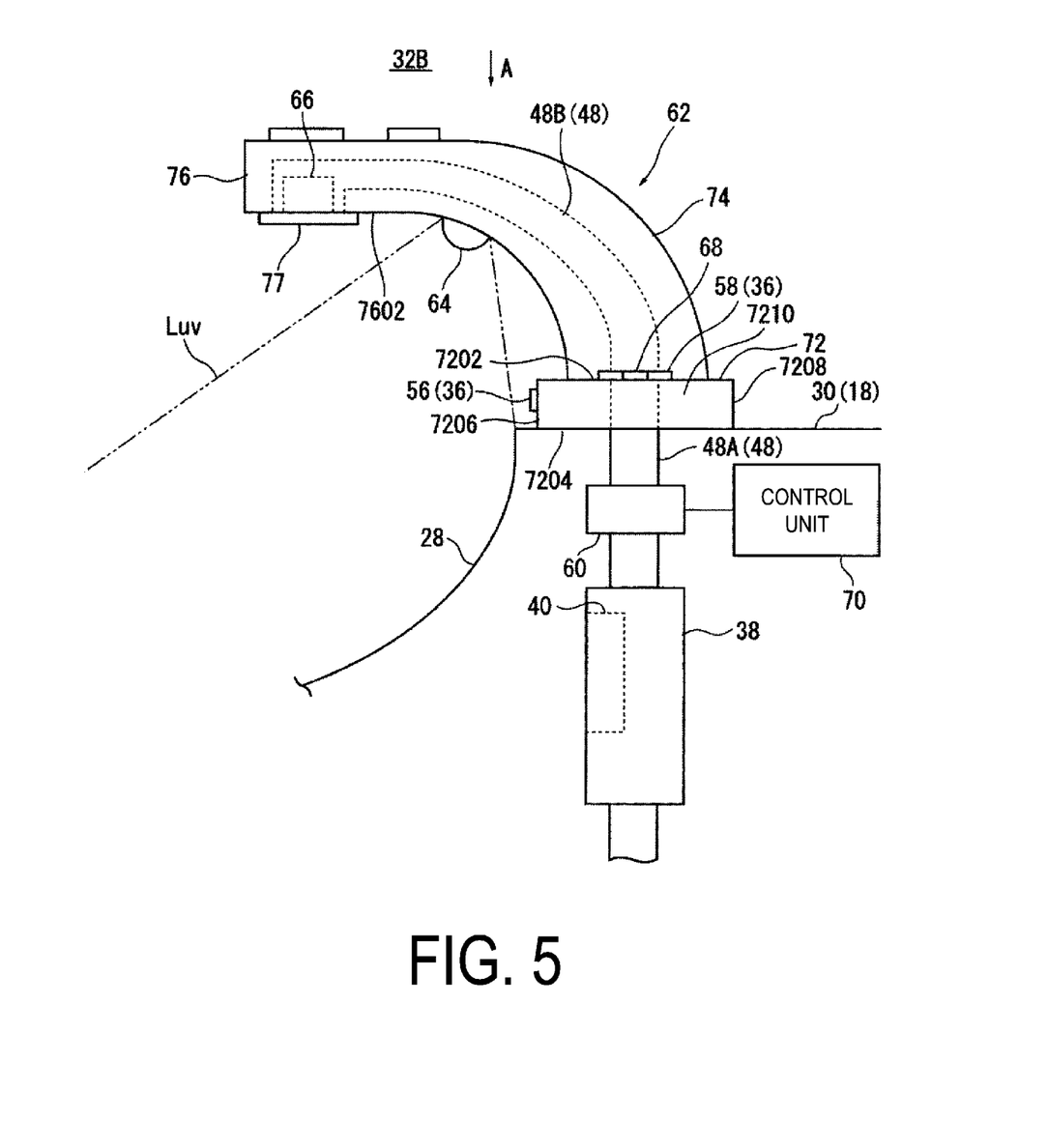
FIG. 5 is a side view of an automatic water faucet apparatus according to a second embodiment.

In the second embodiment, the shape of a faucet 62 differs from that of the first embodiment, and also the second embodiment differs from the first embodiment in that the hot water storage tank 38 is provided outside of the faucet 34, and the hand wash bowl 28 and a water discharge port 77 are irradiated with ultraviolet rays in addition to the hot water storage tank 38.

As illustrated in FIGS. 5 to 8, an automatic water faucet apparatus 32B includes the faucet 62, the detection unit 36, the hot water storage tank 38, the first ultraviolet irradiation unit 40, a second ultraviolet irradiation unit 64, a third ultraviolet irradiation unit 66, a display unit 68, and a control unit 70.

As illustrated in FIG. 5, the faucet 62 discharges water supplied from the water supply source 46 via the water supply channel 48. As in the first embodiment, the water supply channel 48 includes the first water supply channel 48A that is connected to the water supply source 46 and located outside the faucet 62 and the second water supply channel 48B that is provided inside the faucet 62 and connects the first water supply channel 48A and the water discharge port 77 described below.

Figure 6:
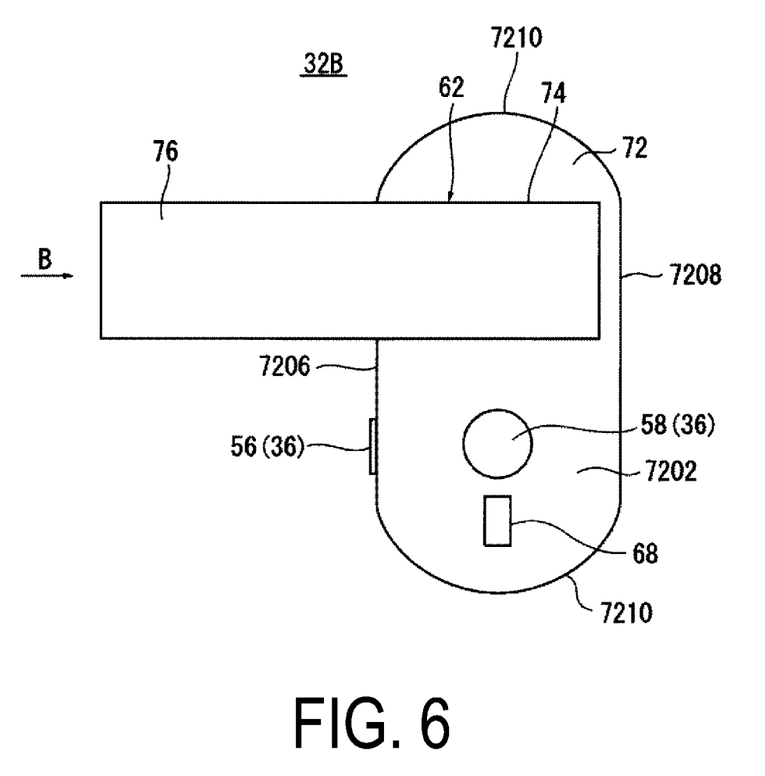
FIG. 6 is a view in the direction of arrow A in FIG. 5.
Figure 7:
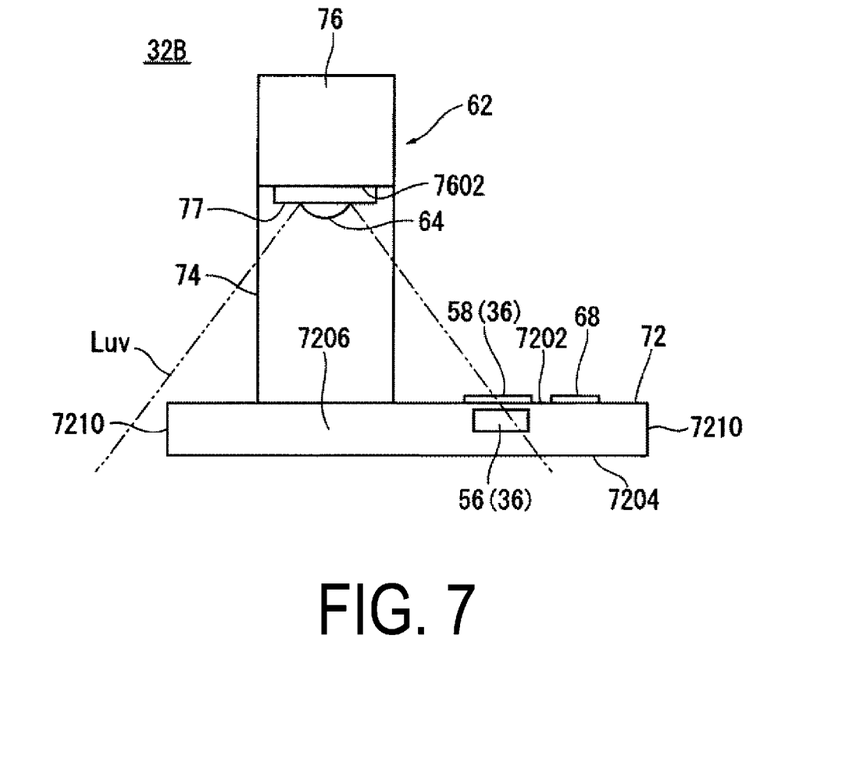
FIG. 7 is a view in the direction of arrow B in FIG. 6.

As illustrated in FIGS. 5, 6, and 7, the faucet 62 includes a board portion 72 attached to the upper surface of the sink 30 or the wall portion in the vicinity of the sink 30, an extending portion 74 extending above the hand wash bowl 28 from the board portion 72, and a water discharge portion 76 that is provided on a tip portion extending in a substantially horizontal direction of the extending portion 74 and includes the water discharge port 77 directed to the inside of the hand wash bowl 28.

Thus, the water discharge port 77 is provided at a location separated upward from the hand wash bowl 28.

Note that as in the first embodiment, the faucet 62 including the board portion 72 is made of various known materials such as metal and synthetic resin.

In the second embodiment, the board portion 72 has a flat long-circle plate shape with a contour larger than the cross-sectional shape of the extending portion 74.

The board portion 72 includes an upper surface 7202 facing upward, a lower surface 7204 facing downward, a front surface 7206 facing the hand wash bowl 28 side, a rear surface 7208 facing in the direction opposite to the front surface 7206, and a pair of curved side surfaces 7210 connecting the upper surface 7202, the lower surface 7204, the front surface 7206, and the rear surface 7208.

The extending portion 74 rises from the upper surface 7202 on one side in the longitudinal direction of the board portion 72.

Note that the board portion 72 and the extending portion 74 may be integrally provided, or the board portion 72 and the extending portion 74 may be provided separately and, for example, the extending portion 74 may be inserted into a hole provided in the board portion 72.

Figure 8:
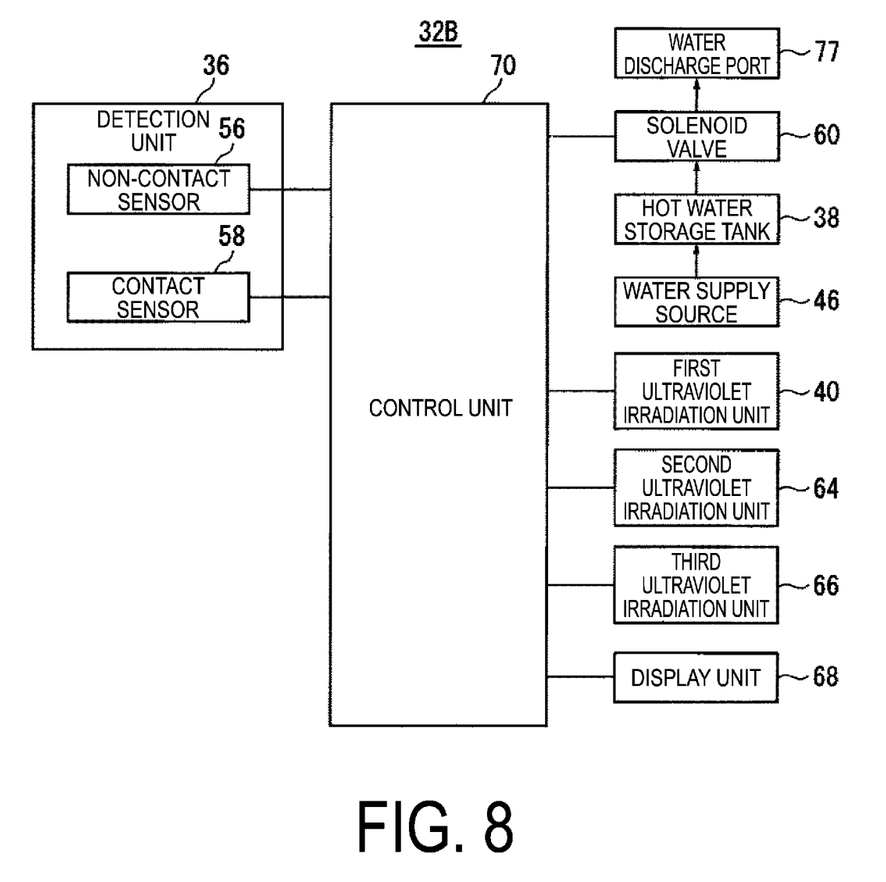
FIG. 8 is a block diagram illustrating a configuration of a control system of the automatic water faucet apparatus according to the second embodiment.

As in the first embodiment, the detection unit 36 includes two sensors, the non-contact sensor 56 and the contact sensor 58.

In the second embodiment, the non-contact sensor 56 is an infrared sensor and is provided on the front surface 7206 on the other side in the longitudinal direction of the board portion 72.

The non-contact sensor 56 is designed to irradiate the forward of the board portion 72 with detection light and reliably irradiate fingers of a user inserted in the hand wash bowl 28 with the detection light.

The contact sensor 58 detects part of a human body when the part of the human body contacts therewith, and in the second embodiment, the contact sensor 58 is a touch switch, and is provided side by side with the extending portion 74 on an upper surface of the board portion 72.

The contact sensor 58 projects upward from the upper surface 7202 of the board portion 72 and is designed to allow a finger of a user to easily contact the contact sensor 58.

As illustrated in FIG. 5, the hot water storage tank 38 heats water supplied to the water supply channel 48 by using a heater, which is not illustrated, and stores hot water. In the second embodiment, the hot water storage tank 38 is provided at a location separated from the faucet 62 and heats the water supplied to the first water supply channel 48A, that is, the hot water storage tank 38 is provided at a location below the sink 30.

As in the first embodiment, the first ultraviolet irradiation unit 40 includes an ultraviolet lamp disposed inside the hot water storage tank 38, and irradiation of ultraviolet rays to the hot water stored in the hot water storage tank 38 and stop of the irradiation are controlled by the control unit 70 described below.

As illustrated in FIGS. 5 and 7, the second ultraviolet irradiation unit 64 irradiates the hand wash bowl 28 with ultraviolet rays Luv.

In the second embodiment, the second ultraviolet irradiation unit 64 includes an ultraviolet lamp provided on a lower surface 7602 of the water discharge portion 76 directed toward the hand wash bowl 28, and irradiation of the ultraviolet rays Luv to the hand wash bowl 28 and stop of the irradiation are controlled by the control unit 70 described below.

As illustrated in FIG. 5, the third ultraviolet irradiation unit 66 irradiates the water discharge port 77 with ultraviolet rays.

In the second embodiment, the third ultraviolet irradiation unit 66 is a column and is disposed in the center of the water discharge port 77 and is provided inside the water discharge port 77 in a state an annular space through which hot water can flow is secured between an outer circumferential surface of the third ultraviolet irradiation unit 66 and an inner circumferential surface of the water discharge port 77.

The third ultraviolet irradiation unit 66 includes an ultraviolet lamp, and irradiation of ultraviolet rays from the outer circumferential surface of the third ultraviolet irradiation unit 66 to the inner circumferential surface of the water discharge port 77 is controlled by the control unit 70 described below.

The display unit 68 indicates that irradiation of ultraviolet rays by the first, second, and third ultraviolet irradiation units 40, 64, and 66 are being performed, and in the second embodiment, the display unit 68 is provided side by side with the contact sensor 58 at a location on the side of the contact sensor 58 on the upper surface 7202 of the board portion 72.

The display unit 68 includes an LED lamp, and lighting of the LED lamp indicates that irradiation of ultraviolet rays is being performed, and turning off of the LED lamp indicates that the irradiation of ultraviolet rays is stopped.

The control unit 70 may be provided in the faucet 62, but in the second embodiment, the control unit 70 is provided at a location below the counter table 18 in the vicinity of the faucet 62.

The control unit 70 is connected to the detection unit 36 via a cable, which is not illustrated, and switches between discharge and stop of water from the water discharge port 77 based on a detection signal supplied via the cable.

As illustrated in FIG. 5, in the second embodiment, the solenoid valve 60 is provided at a location of the first water supply channel 48A between the hot water storage tank 38 and the faucet 62, and when the control unit 70 receives the detection signal indicating that part of a human body has been detected by the detection unit 36, the solenoid valve 60 is opened for a first predetermined time, which is preliminarily set, to discharge water from the water discharge port 77, and the solenoid valve 60 is closed when the first predetermined time has elapsed.

Further, the control unit 70 controls irradiation of ultraviolet rays by the first, second, and third ultraviolet irradiation units 40, 64, and 66, and stop of the irradiation based on the detection signal output from the detection unit 36.

In the second embodiment, the control unit 70 is configured to cause the first, second, and third ultraviolet irradiation units 40, 64, and 66 to perform irradiation of ultraviolet rays for a second predetermined time, which is preliminarily set, when the water discharge port 77 stops water.

This second predetermined time is set to time sufficient to sufficiently disinfect the hot water in the hot water storage tank 38, disinfect the hand wash bowl 28, and disinfect the inner circumferential surface of the water discharge port 77.

In the second embodiment, a case in which the predetermined time for irradiating ultraviolet rays is set to the same second predetermined time for all of the first, second, and third ultraviolet irradiation units 40, 64, and 66 is described. However, the predetermined time for irradiating ultraviolet rays may be different for each of the first, second, and third ultraviolet irradiation units 40, 64, and 66.

Further, the control unit 70 lights the display unit 68 during the second predetermined time at which irradiation of ultraviolet rays by the first, second, third ultraviolet irradiation units 40, 64, and 66 are performed, and indicates that irradiation of ultraviolet rays is being performed. When the second predetermined time has elapsed, the control unit 70 turns off the display unit 68 and indicates that irradiation of ultraviolet rays is stopped.

Figure 9:
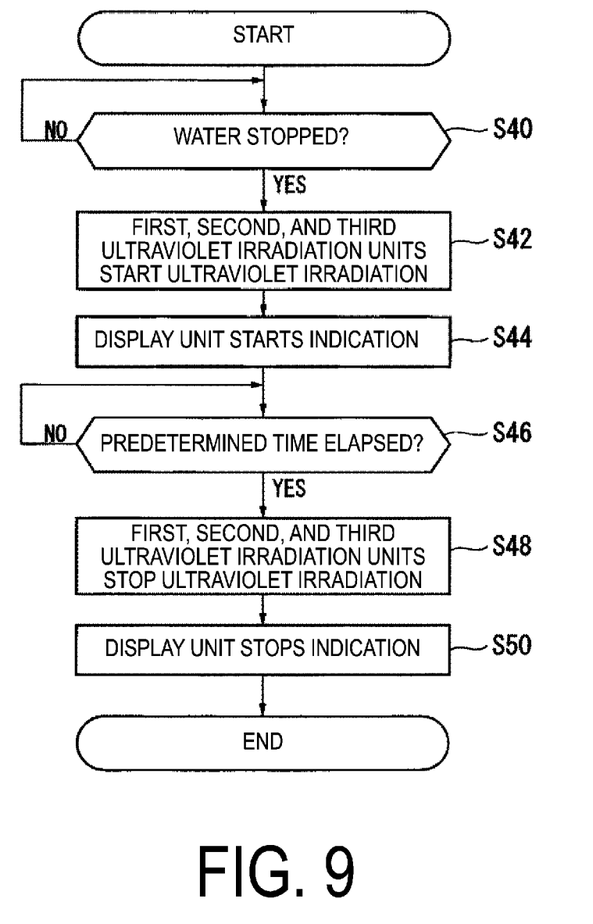
FIG. 9 is a flowchart illustrating an operation of the automatic water faucet apparatus according to the second embodiment.

Next, control of the first, second, and third ultraviolet irradiation units 40, 64, and 66 by the control unit 70 is described with reference to the flow chart of FIG. 9.

First, the control unit 70 determines whether water is stopped based on presence of the detection signal from the detection unit 36 (step S40).

When YES is determined in step S40, water is stopped, and thus irradiation of ultraviolet rays by the first, second, and third ultraviolet irradiation units 40, 64, and 66 are performed (step S42).

When NO is determined in step S40, water is being discharged, and thus, the process returns to step S40 without performing ultraviolet irradiation by the first, second, and third ultraviolet irradiation units 40, 64, and 66.

This is because, while water is being discharged, an effect of disinfection is less effective even when hot water flowing from the hot water storage tank 38 toward the water discharge port 77 is irradiated with ultraviolet rays by the first ultraviolet irradiation unit 40.

Further, this is because, while water is being discharged, an effect of disinfecting the hand wash bowl 28 is less effective even when the hand wash bowl 28 is irradiated with ultraviolet rays by the second ultraviolet irradiation unit 64 while hot water is flowing onto the hand wash bowl 28.

Furthermore, this is because, while wateris being discharged, an effect of disinfecting the inner circumferential surface of the water discharge port 77 is less effective even when irradiation of ultraviolet rays from the outer circumferential surface of the third ultraviolet irradiation unit 66 to the inner circumferential surface of the water discharge port 77 is performed while hot water is discharged from the water discharge port 77.

Further, the control unit 70 lights the display unit 68 at the same time as irradiation of ultraviolet rays by the first, second, and third ultraviolet irradiation units 40, 64, and 66 and causes the display unit 68 to indicate that irradiation of ultraviolet rays is being performed (step S44).

Next, the control unit 70 determines whether the irradiation of ultraviolet rays by the first, second, and third ultraviolet irradiation units 40, 64, and 66 has performed for the second predetermined time (step S46).

When NO is determined in step S46, the control unit 70 returns to step S46 and the irradiation of ultraviolet rays continues.

When YES is determined in step S46, the control unit 70 causes the first, second, and third ultraviolet irradiation units 40, 64, and 66 to stop the irradiation of ultraviolet rays (step S48), at the same time causes the display unit 68 to stop the indication (step S50), and terminates a series of operations.

Note that in the second embodiment, every time the water is stopped, the first, second, and third ultraviolet irradiation units 40, 64, and 66 perform irradiation of ultraviolet rays and disinfect the hot water in the hot water storage tank 38, the hand wash bowl 28, and the water discharge port 77, respectively.

However, when it is expected that water is not discharged for a long time after this disinfection is completed and the water is stopped for a long time, it is preferable to mandatorily disinfect the inside of the hot water storage tank 38, the hand wash bowl 28, and the water discharge port 77.

In this case, the control unit 70 may determine whether duration of the state of water stopped has passed a third predetermined time, which is preliminarily set. When determining that the third predetermined time has elapsed, the control unit 70 only needs to perform the processes of from steps S42 to S50. Such processes are advantageous in reliably disinfecting the hot water in the hot water storage tank 38, the hand wash bowl 28, and the inner circumferential surface of the water discharge port 77 when hot water is not discharged for a long time.

According to the second embodiment, it is needless to say that the same effects as those of the first embodiment are achieved, and the hot water storage tank 38 is provided at a location separated from the faucet 62, thus it is advantageous in making the faucet 62 more compact and in improving flexibility of layout and aesthetics of the automatic water faucet apparatus 32B.

Further, according to the second embodiment, the second ultraviolet irradiation unit 64 that irradiates the hand wash bowl 28 with the ultraviolet rays Luv is provided, allowing bacteria in the hand wash bowl 28 to which dirt and moisture easily adhere to be prevented from growing and advantageously maintaining hygiene of the hand wash bowl 28.

Furthermore, applying this automatic water faucet apparatus 32B to the aircraft lavatory unit 10 is advantageous in maintaining and managing hygienic environment of the aircraft lavatory unit 10 and in increasing product value of the aircraft lavatory unit 10.

Further, according to the second embodiment, since the second ultraviolet irradiation unit 64 is provided on the lower surface 7602 of the water discharge portion 76 directed toward the hand wash bowl 28, a wide range of the hand wash bowl 28 can be irradiated with the ultraviolet rays Luv, and it is more advantageous in maintaining hygiene of the hand wash bowl 28.

Furthermore, according to the second embodiment, the third ultraviolet irradiation unit 66 that irradiates the water discharge port 77 with ultraviolet rays is provided, allowing bacteria in the water discharge port 77 to be prevented from growing and advantageously maintaining hygiene of the hot water to be discharged.

Further, in the second embodiment, since the display unit 68 that indicates that irradiation of ultraviolet rays by the first, second, and third ultraviolet irradiation units 40, 64, and 66 are being performed is provided, the user can visually recognize the display unit 68 and understand that the hot water stored in the hot water storage tank 38, the hand wash bowl 28, and the inner circumferential surface of the water discharge port 77 are each disinfected. Accordingly, the user can be encouraged to use the automatic water faucet apparatus 32B after the indication by the display unit 68 has stopped. Accordingly, the automatic water faucet apparatus 32B can be used after confirming that hygiene of the hot water stored in the hot water storage tank 38, the hand wash bowl 28, and the inner circumferential surface of the water discharge port 77 is maintained, which is advantageous in improving convenience.

Note that in the second embodiment, the case in which both the second ultraviolet irradiation unit 64 and the third ultraviolet irradiation unit 66 are provided in addition to the first ultraviolet irradiation unit 40 is described. However, any one of the second ultraviolet irradiation unit 64 and the third ultraviolet irradiation unit 66 may be provided in addition to the first ultraviolet irradiation unit 40.

However, when provided as in the second embodiment, disinfection of bacteria can be performed for all of the hot water storage tank 38, the hand wash bowl 28, and the water discharge port 77, and thus, it is advantageous in maintaining hygiene of the automatic water faucet apparatus 32B and the hand wash bowl 28.

The invention claimed is:

1. An automatic water faucet apparatus configured to discharge and stop water by detecting part of a human body, the automatic water faucet apparatus comprising:
    a faucet comprising a water discharge port and attached to a sink;
    a hot water storage tank configured to heat water supplied to a water supply channel communicating with the water discharge port and store hot water, the hot water storage tank being provided inside the faucet; and
    a first ultraviolet irradiation unit configured to irradiate the hot water stored in the hot water storage tank with ultraviolet rays.

2. The automatic water faucet apparatus according to claim 1, wherein
    the water supply channel comprises a first water supply channel located outside the faucet and a second water supply channel provided inside the faucet and connecting the first water supply channel and the water discharge port, and
    the hot water storage tank heats water supplied to the second water supply channel.

3. The automatic water faucet apparatus according to claim 2, further comprising:
    a detection unit configured to detect part of a human body; and
    a control unit configured to switch between discharge and stop of water from the water discharge port based on a detection signal output from the detection unit and to control irradiation of ultraviolet rays by the first ultraviolet irradiation unit and stop of the irradiation, wherein
    the control unit causes the first ultraviolet irradiation unit to perform irradiation of ultraviolet rays for a predetermined time when the water discharge port stops water.

4. The automatic water faucet apparatus according to claim 3, further comprising:
    a display unit configured to indicate that irradiation of ultraviolet rays by the first ultraviolet irradiation unit is being performed.

5. The automatic water faucet apparatus according to claim 4, wherein
    the sink comprises a hand wash bowl, and
    a second ultraviolet irradiation unit configured to irradiate the hand wash bowl with ultraviolet rays is provided.

6. The automatic water faucet apparatus according to claim 5, wherein the display unit indicates that irradiation of ultraviolet rays by the second ultraviolet irradiation unit is being performed.

7. The automatic water faucet apparatus according to claim 6, wherein
    the faucet comprises a water discharge portion provided with the water discharge port facing the hand wash bowl at a location separated upward from the sink, and
    the second ultraviolet irradiation unit is provided on a lower surface of the water discharge portion directed toward the hand wash bowl.

8. The automatic water faucet apparatus according to claim 7, further comprising:
    a third ultraviolet irradiation unit configured to irradiate the water discharge port with ultraviolet rays.

9. The automatic water faucet apparatus according to claim 8, wherein the display unit indicates that irradiation of ultraviolet rays by the third ultraviolet irradiation unit is being performed.

10. The automatic water faucet apparatus according to claim 1, further comprising:
    a detection unit configured to detect part of a human body; and
    a control unit configured to switch between discharge and stop of water from the water discharge port based on a detection signal output from the detection unit and to control irradiation of ultraviolet rays by the first ultraviolet irradiation unit and stop of the irradiation, wherein
    the control unit causes the first ultraviolet irradiation unit to perform irradiation of ultraviolet rays for a predetermined time when the water discharge port stops water.

11. The automatic water faucet apparatus according to claim 1, further comprising:
    a display unit configured to indicate that irradiation of ultraviolet rays by the first ultraviolet irradiation unit is being performed.

12. The automatic water faucet apparatus according to claim 1, wherein
    the sink comprises a hand wash bowl, and
    a second ultraviolet irradiation unit configured to irradiate the hand wash bowl with ultraviolet rays is provided.

13. The automatic water faucet apparatus according to claim 1, further comprising:
    a third ultraviolet irradiation unit configured to irradiate the water discharge port with ultraviolet rays.

* * * * *